United States Patent [19]

Sakai et al.

[11] Patent Number: 4,652,640

[45] Date of Patent: Mar. 24, 1987

[54] CRYSTALLINE MALTOPENTAOSE AND PROCESS FOR PRODUCING THE SAME

[75] Inventors: Shuzo Sakai; Takashi Shibuya; Toshio Miyake, all of Okayama, Japan

[73] Assignee: Hayashibara Seibutsu Kagaku Kenkyujo Kabushiki Kaisha, Okayama, Japan

[21] Appl. No.: 764,176

[22] Filed: Aug. 9, 1985

[30] Foreign Application Priority Data

Aug. 14, 1984 [JP] Japan .................. 59-169599

[51] Int. Cl.$^4$ .......................... C07H 1/00; C07H 3/06
[52] U.S. Cl. ...................... 536/124; 536/1.1; 536/127
[58] Field of Search .............. 536/1.1, 124, 127; 514/53

[56] References Cited

U.S. PATENT DOCUMENTS

| | | | |
|---|---|---|---|
| 3,879,263 | 4/1975 | Adams. | |
| 4,147,860 | 4/1979 | Farnham et al. | 536/119 |
| 4,408,041 | 10/1983 | Hirao et al. | 536/4.1 |
| 4,487,198 | 1/1984 | Miyake et al. | 127/46.3 |
| 4,521,252 | 1/1985 | Miyake et al. | 127/46.3 |

FOREIGN PATENT DOCUMENTS 0030911  3/1981  Japan ..................... 514/53

OTHER PUBLICATIONS

Saito, Narimasa, "Evaluation of Maltopentaose (G$_5$) as a Substrate for α-Amylase Determination in Serum.", J. Jap. Soc. Starch Sci., 29, 2, 153–160, (1982).

Wako, K., "Studies on the Maltooligosaccharide-Producing Amylases", J. Jap. Starch Sci., 28, 215–218, (1981).

"Dictionary of Organic Compounds", vol. 4, p. 2049, (1965), Eyre & Spottiswoode Publishers, Ltd.

*Primary Examiner*—Johnnie R. Brown
*Attorney, Agent, or Firm*—Browdy and Neimark

[57] ABSTRACT

Maltopentaose is crystallized from a supersaturated solution of a high-purity maltopentaose, obtained by fractionation of a feed solution, containing maltopentaose along with additional higher and lower maltooligosaccharides, using a strongly-acidic cation exchange resin in a salt form (e.g. alkali- or alkaline-metal form). Crystalline maltopentaose is non-hygroscopic and non-deliquescent. A pulverulent solid containing crystalline maltopentaose is found substantially non-hygroscopic. Crystalline maltopentaose is favorably usable as the substrate to assay serum amylase. Crystalline maltopentaose and pulverulent solid containing the same are favorably usable to produce foodstuffs, pharmaceuticals, cosmetics, and chemicals.

7 Claims, 5 Drawing Figures

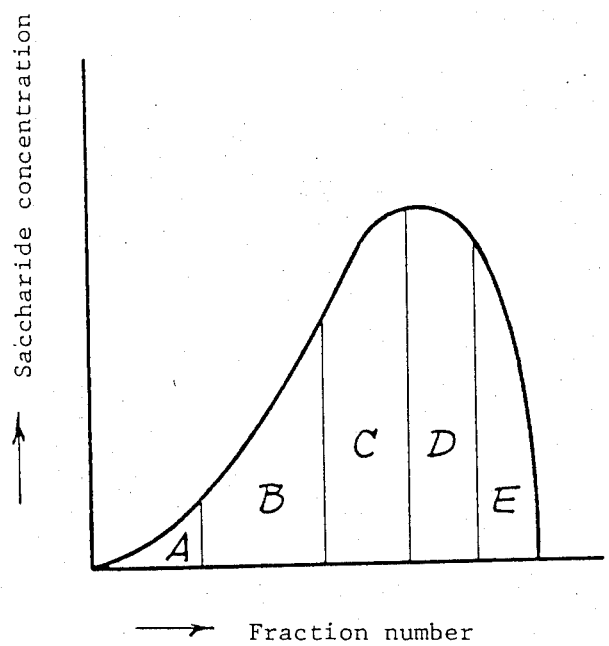

CRYSTALLINE MALTOPENTAOSE AND PROCESS FOR PRODUCING THE SAME

FIELD OF THE INVENTION

The present invention relates to crystalline maltopentaose and its production.

DEFINITIONS

Percentages are given by weight based on the weight of dry solids, unless specified otherwise.

Saccharide L means a saccharide or a saccharide mixture with a degree of glucose polymerization of 6 or higher.

Saccharide S means a saccharide or a saccharide mixture with a degree of glucose polymerization of 4 or lower.

Degree of cross-linking is defined as the ratio of divinylbenzene to the total amount of the monomers used to produce a styrene-divinylbenzene copolymer resin, expressed in percentage.

In the elution pattern obtained with such resin, "fraction A" means the fraction rich in saccharide L; "fraction B", the fraction rich in saccharide L but highly contaminated with maltopentaose; "fraction C", the fraction rich in maltopentaose; "fraction D", the fraction rich in maltopentaose but highly contaminated with saccharide S; and "fraction E", the fraction rich in saccharide S.

DESCRIPTION OF THE PRIOR ARTS

As described in Japan Patent Kokai No. 56,998/75, and *Journal of the Japanese Society of Starch Science*, Vol. 29, No. 2, pp. 153–160 (1982), maltopentaose is lately used as a substrate to assay serum amylase.

Commercialized maltopentaose with a purity lower than about 94%, however, has the disadvantage that it must be handled with a possible religious care because it is non-crystalline, amorphous, pulverulent and highly hygroscopic.

As is evident from the description in *Journal of the Japanese Society of Starch Science*, Vol. 28, No. 3, pp. 215–218 (1981) that the crystalline maltooligosaccharides so far known are only $G_1$ and $G_2$, crystalline maltopentaose is unknown.

BRIEF DESCRIPTION OF THE DRAWINGS

FIG. 5 shows an elution pattern of the feed solution, obtained during high-purity maltopentaose production.

DETAILED DESCRIPTION OF THE INVENTION

The present inventors investigated various means to obtain crystalline maltopentaose which is free of the above mentioned disadvantages of conventional maltopentaose. As the result, we have found a non-hygroscopic crystalline maltopentaose, and developed a process to produce the crystalline maltopentaose, This is the present invention.

More particularly, we prepared a crystalline maltopentaose seed as follows: A column of a strongly-acidic cation exchange resin in salt form was successively admitted with predetermined volumes of a saccharide mixture solution, containing maltopentaose and saccharides L and S, and water to effect fractionation. The obtained effluents were successively separated into fractions A, B, C, D, and E, followed by recovery of fraction C with a maltopentaose purity of 96.7%. Fraction C was then decolored with activated carbon, deionized with ion exchange resins in H- and OH-forms, concentrated to 75%, and placed in a glass beaker. Upon 4 month-standing at about 25° C., crystals appeared on the inside wall of the glass beaker. The crystals were used as the seed.

An 80% concentrate of fraction C was added with the seed crystals, and then crystallized under gentle stirring conditions. A crystalline maltopentaose with a purity of 99.6% was separated from the resultant crystal suspension.

The physicochemical properties of the crystalline maltopentaose are as follows:

(1) Specific rotation $[\alpha]_D^{25}$ is plus 181.8° (C=1.0, in $H_2O$).

(2) uv-Absorption spectrum

An aqueous solution of crystalline maltopentaose exhibits no characteristic uv-absorption.

(3) Infrared spectrum

Figure 1:
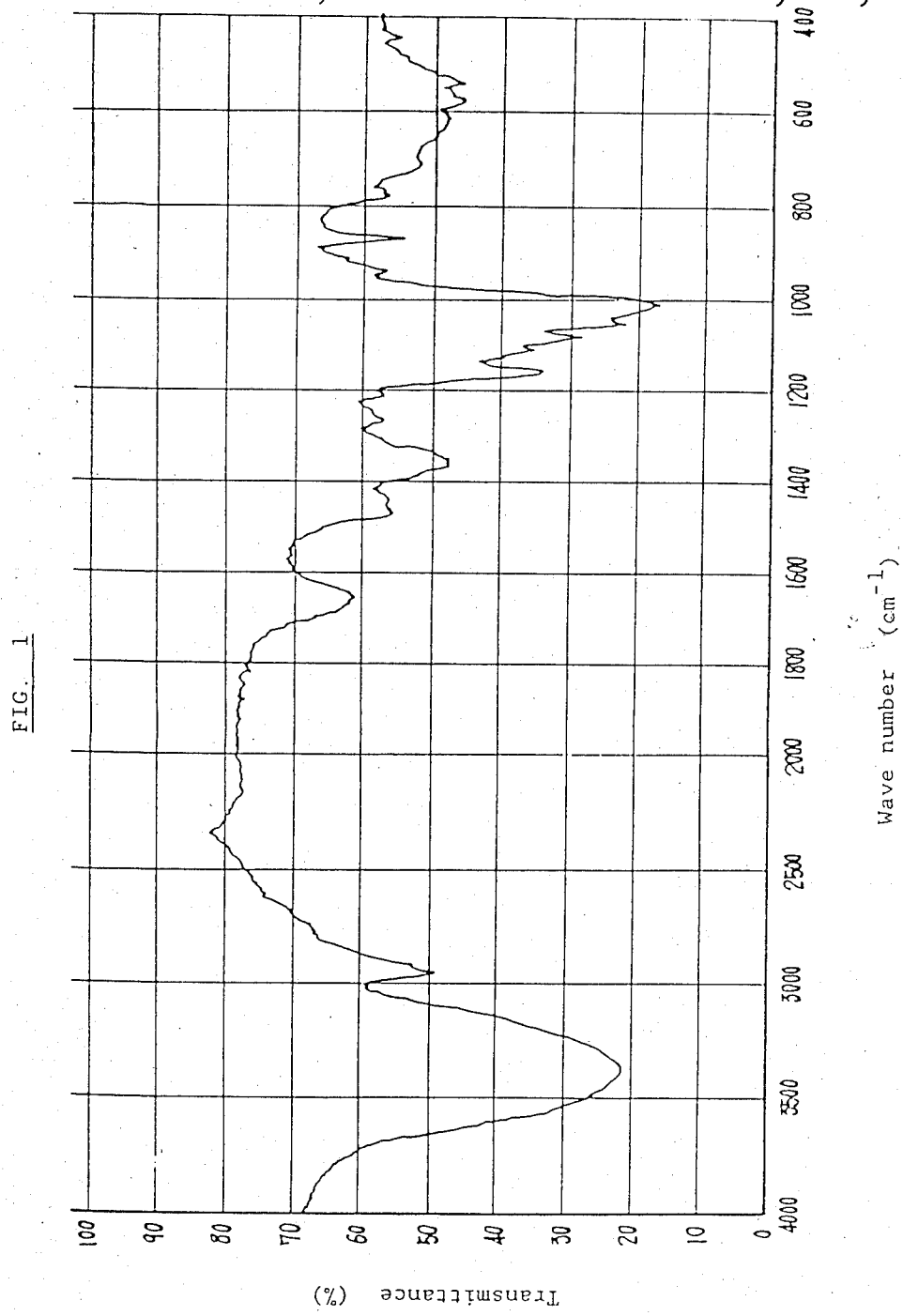
FIG. 1 shows an infrared spectrum of crystalline maltopentaose.

Five mg of pulverulent crystalline maltopentaose and 220 mg of dehydrated KBr were mixed by stirring to obtain a transparent tablet, about 0.6 mm thick, which was then subjected to infrared spectrometry. The result is given in FIG. 1.

(4) Melting point

91°–93° C. when subjected to thermal analysis.

(5) Heat of dissolution

Upon thermal analysis, about 18 cal/g is endothermically absorbed.

(6) Solubility

One hundred g of water dissolves up to 96.3 g of anhydrous crystalline maltopentaose at 25° C.

(7) Appearance and properties

Figure 2:
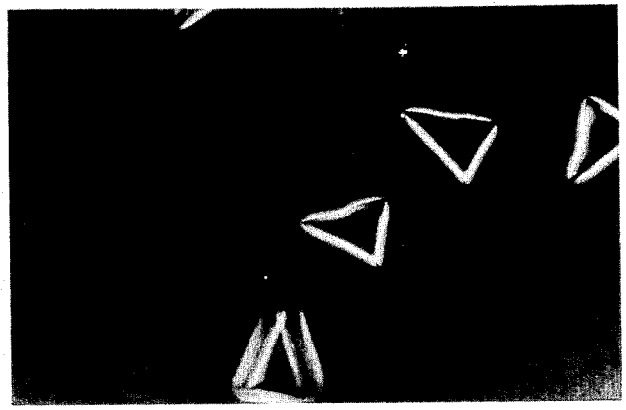
FIG. 2 shows a photomicrographic view of crystalline maltopentaose.

Colorless, transparent crystal. Microcrystal is a white, odorless, slightly sweet, pulverulent solid. Non-hygroscopic and non-deliquescent. FIG. 2 photomicrographically shows a crystallization in 70% aqueous maltopentaose solution. Its aqueous solution is neutral or slightly acidic.

(8) Solubility in solvent

Readily dissolvable in water, 0.1N NaOH, and 0.1N HCl. Scarcely dissolvable in methanol and ethanol. Insoluble in chloroform and ethyl acetate.

(9) Color reaction

Turns green by anthrone-sulfuric acid reaction. Fehling's reaction, positive. Iodine reaction, negative.

(10) Saccharide components (a) Paper- and gas-chromatographic analyses confirm that the hydrolysate, obtained by hydrolysis with 1N sulfuric acid, consists of D-glucose.

(b) Complete methylation and subsequent gas chromatographic analysis confirm the ratio of 1,2,3,6-tetra-O-methyl-D-glucose, 2,3,6-tri-O-methyl-D-glucose, and 2,3,4,6-tetra-O-methyl-D-glucose as 1:3:1.

(c) High specific rotation, i.e. $[\alpha]_D^{25}$ of plus 181.8°, and the infrared absorption peak near to 840 $cm^{-1}$ elucidates that the saccharide components are linked in an α-fashion.

(d) Upon paper- and high-pressure liquid-chromatographic analyses, the crystal is detected at the same retention time as observed with a commercialized amorphous maltopentaose used as the authentic sample.

(11) x-Ray diffraction

An x-ray diffraction figure of the crystalline maltopentaose, determined in accordance with the procedure as described by F. H. Stodola et al., in *Journal of the American Chemical Society*, Vol. 78, pp. 2514–2518 (1956), is shown as FIG. 3. The x-ray diffractometer employed was "GEIGERFREX RAD-II B" using CuK$\alpha$ ray, a product of Rigaku Corporation, Chiyoda-ku, Tokyo, Japan. As the control, an x-ray diffraction figure of an amorphous pulverulent maltopentaose, obtained by completely dissolving crystalline maltopentaose in hot water, and heat-drying the resultant solution, is shown as FIG. 4. As is evident from FIG. 3, the x-ray diffraction analysis of crystalline maltopentaose with CuK$\alpha$ ray gives predominant diffraction angles ($2\theta$) of 9.7°, 15.8°, 16.2°, 17.2°, and 23.7°.

From these evidences, it can be seen that the crystal is a so far unknown crystalline maltopentaose with a non-hygroscopic property.

The production of crystalline maltopentaose and pulverulent solid containing the same will hereinafter be described.

Any high-purity maltopentaose solution can be used regardless of its method of production, as long as the solution is supersaturated and maltopentaose can be crystallized from the solution.

High-purity maltopentaose can be produced as follows: For example, a saccharide mixture solution containing maltopentaose, obtained by liquefying a starch suspension while heating, and hydrolyzing the resultant starch solution with $\alpha$-amylase (EC 3.2.1.1), is admitted to a column of a strongly-acidic cation exchange resin in salt form, and then eluted from the column with water into fractions A, B, C, D, and E in accordance with the elution pattern as shown in FIG. 5. Fraction C with a maltopentaose purity of about 85% or higher can be favorably used to produce crystalline maltopentaose.

Fractions B and E can be admitted to the column along with a saccharide mixture solution containing maltopentaose. In particular, a procedure wherein fraction B, the saccharide mixture solution containing maltopentaose, and fraction D are successively admitted is desirable because maltopentaose of a higher concentration can be recovered in a higher yield.

The strongly-acidic cation exchange resin in salt form is one or more styrene-divinylbenzene copolymer resins, desirably, with a degree of cross-linking of 6% or lower, which bear sulphonic groups in an alkali-metal- or an alkaline earth metal-form, such as Na$^+$, K$^+$, Ca$^{2+}$, or Mg$^{2+}$. Examples of commercialized resins are "Dowex 50WX1", "Dowex 50WX2" and "Dowex 50WX4", products of Dow Chemicals Co., Midland, MI, USA; "Amberlite CG-120", a product of Rohm & Haas Co., Philadelphia, PA, USA; "XT-1022E" and "XT-1007", products of Tokyo Chemical Industries, Kita-ku, Tokyo, Japan; and "Diaion SK 1B", "Diaion SK 102", "Diaion SK 104", and "Diaion SK 106", products of Mitsubishi Chemical Industries Ltd., Tokyo, Japan. The fractionation can be carried out by the fixed bed-, moving bed-, or simulated moving bed-method.

To crystallize maltopentaose, the high-purity maltopentaose thus obtained is prepared into an about 65–95% aqueous syrup which is then adjusted within a temperature range of 0°–95° C., the range where the syrup does not freeze and the heat loss during processing is relatively small. The saturation degree and viscosity of the syrup may be regulated by the presence of, for example, methanol, ethanol, acetone, etc. Generally, a saturated maltopentaose solution, prewarmed to a relatively high temperature, i.e. 40°–95° C., is fed to a crystallizer, added with the seed in an amount of, desirably, 0.1–20%, and gradually cooled while accelerating maltopentaose crystallization by stirring.

Examples of the procedures employed to prepare the resultant crystal suspension into pulverulent solid include conventional crystal separation-, block-pulverization-, fluidized-bed granulation-, and spray-drying-methods.

The crystal separation method, for example, usually comprises feeding the resultant crystal suspension to a basket-type centrifuge, separating the crystal suspension into crystalline maltopentaose and mother liquor, and, if desired, washing the crystalline maltopentaose by spraying it with a small amount of water or a chilled alcoholic solution to obtain crystalline maltopentaose in a higher purity.

Since in the other three methods the mother liquor is not separated from the crystallized maltopentaose, these methods do not lead to a product of a higher maltopentaose purity, but a higher yield. The pulverulent product, obtained by any of these methods, contains crystalline maltopentaose, and, inevitably, small amounts of additional saccharides such as maltohexaose, maltotetraose, and multotriose.

In the spray-drying method, a crystal suspension with a concentration of about 70–85%, in which crystallization has been effected up to about 25–60%, is spray-dried through a nozzle using a high-pressure pump, and the obtained pulverulent product is then dehydrated in a hot air stream at a temperature, e.g. 60°–100° C., which does not melt the crystalline maltopentaose. Subsequently, the pulverulent product is aged in a 30°–60° C. air for about 1–20 hours to obtain a substantially non-hygroscopic pulverulent product.

In the block-pulverization method, generally a crystalline suspension with a moisture content of 5–15%, in which crystallization has been effected up to about 10–60%, is solidified into block by allowing it to stand for 0.5–5 days. A substantially non-hygroscopic pulverulent product is obtained by crushing and/or cutting the crystalline block, and dehydrating the resultant product.

Crystalline maltopentaose and pulverulent solid containing the same are both substantially non-hygroscopic, freely-flowing, and easily handleable without fear of caking or consolidation. Thus, in addition to the uses as chemical reagent and substrate for assaying amylase, these products can be favorably used to produce foodstuffs, pharmaceuticals, cosmetics, and chemicals. Since these products are free of starch-odor, and exhibit an appropriate viscosity and a slight sweetness, they can be favorably used to produce diets such as protein-free high-calorie diet, as well as to produce foodstuffs and pharmaceuticals for oral administration in granule, cube, block, or tablet, in combination with filler, vehicle, and/or binder. In addition, since the slight sweetness, as well as the viscosity- and gloss-imparting properties, well harmonizes with sour-, salty-, astringent-, and delicious-substances, and the products per se are highly acid- and heat-resistant, the products can be favourably used for seasoning and/or improving foodstuffs, e.g. seasonings, confectioneries in general, frozen desserts, processed agricultural products, processed meat products, processed marine products, milk products, liquors, soft drinks, instant foodstuffs, etc.

The production of material high-purity maltopentaose will hereafter be explained with reference to the following experiments.

EXPERIMENT 1

Feed solution for high-purity maltopentaose production

A 6% starch suspension was gelatinized by heating, adjusted to pH 4.5 and 50° C., added with isoamylase (2,500 units/g starch), commercialized by Hayashibara Biochemical Laboratories, Inc., Okayama, Japan, and subjected for twenty hours to the action of the isoamylase. The reaction mixture was adjusted to pH 6.0, autoclaved at 120° C. for ten minutes, cooled to 45° C., added with "Termamyl 60 L" (150 units/g starch), an α-amylase commercialized by Novo Industri A/S, Copenhagen, Denmark, and subjected for twenty-four hours to the action of the α-amylase. The reaction mixture was autoclaved at 120° C. for twenty minutes, cooled, and purified in conventional manner by decoloring with activated carbon, and deionizing with ion exchange resins in H- and OH-forms to obtain a 55% saccharide mixture solution in a yield of about 91%.

The saccharide mixture solution was composed of 47.5% saccharide S, 40.3% maltopentaose, and 12.2% saccharide L.

EXPERIMENT 2

Effect of strongly-acidic cation exchange resin on fractionation of the feed solution The effects of cross-linking defree was studied with the saccharide mixture solution obtained in Experiment 1.

Several commercialized strongly-acidic cation exchange resins in Na+ form, as listed in Table I, were sieved to give those with a mean particle size within 0.1–0.3 mm, prior to their use.

Each resin was packed in a 2.2 cm jacketed stainless steel column to give the bed depth of 10 m. While keeping the inside column temperature at 70° C., the column was admitted first with 40% feed solution in an amount of 10 v/v % to the bed volume, then with 70° C. water at a space velocity of 0.4, followed by successive separation of the resultant effluents. Just before the elution of the saccharides was completed, the obtained fractions were successively recycled to the column, followed by admittance of a balancing amount of hot water. Upon five-cycle repetitions of these operations, the effluents were successively separated into fractions A, B, C, D, and E, followed by the recovery of fraction C with a maltopentaose purity of 90% or higher.

The recovery yield of maltopentaose was determined as the percentage of the maltopentaose content in fraction C to the maltopentaose content in the used feed solution.

TABLE I

| Cross-linking degree of the tested resins | | |
|---|---|---|
| Degree of cross-linking | Trade name of resin | Resin maker |
| 1% | Dowex 50WX1 | Dow Chemicals Co. |
| 2% | Diaion SK102 | Mitsubishi Chemical Industries Ltd. |
| 4% | Dowex 50WX4 | Dow Chemicals Co. |
| 6% | Diaion SK106 | Mitsubishi Chemical |

TABLE I-continued

| Cross-linking degree of the tested resins | | |
|---|---|---|
| Degree of cross-linking | Trade name of resin | Resin maker |
| | | Industries Ltd. |
| 8% | Dowex 50WX8 | Dow Chemicals Co. |
| 10% | Diaion SK110 | Mitsubishi Chemical Industries Ltd. |
| 12% | Diaion SK112 | Mitsubishi Chemical Industries Ltd. |

The results are given in Table II.

These evidences show that the desirable degree of cross-linking is 6% or lower.

TABLE II

| Degree of cross-linking and recovery yield of maltopentaose | |
|---|---|
| Degree of cross-linking (%) | Recovery yield of maltopentaose (%) |
| 1 | 82 |
| 2 | 93 |
| 4 | 94 |
| 6 | 81 |
| 8 | 15 |
| 10 | lower than 5 |
| 12 | lower than 5 |

The invention will be more clearly understood with reference to the following examples.

EXAMPLE 1

Crystalline maltopentaose

The saccharide mixture solution with a maltopentaose purity of 40.3%, prepared in Experiment 1, was used as the feed solution. "XT-1007 (Na+)", a strongly-acidic cation exchange resin in an alkali metal form, with a degree of cross-linking of 6%, commercialized by Tokyo Chemical Industries, Kita-ku, Tokyo, Japan, was chosen, and packed in aqueous suspension in four 5.4 cm jacketed stainless steel columns to give respective bed depth of 5 m. The four columns were cascaded to give a total bed depth of 20 m. While keeping the inside column temperature at 55° C., the feed solution was admitted to the columns in an amount of 5 v/v % to the bed volume, and fractionated by passing 55° C. water at a space velocity of 0.16. Thereafter, the resultant fractions were successively recycled to the column for additional twice similarly as above, followed by the recovery of fraction C with the maltopentaose content of 96.7%. Fraction C was purified by decoloring with activated carbon and deionizing with ion exchange resins in H- and OH-forms, concentrated to 75%, and placed in a glass beaker. Upon four month-standing at about 25° C., maltopentaose was crystallized on the inside wall of the glass beaker. The crystal was then added as the seed in an amount of 4% to an about 50° C. aqueous solution obtained by concentrating fraction C to 80%, and crystallized under gentle stirring. The crystallized maltopentaose was separated from the resultant crystal suspension, and washed with a small amount of a chilled aqueous alcoholic solution to obtain a crystalline maltopentaose with a purity of 99.6%.

The crystalline maltopentaose exhibited no hygroscopicity even under ambient conditions.

Figure 3:
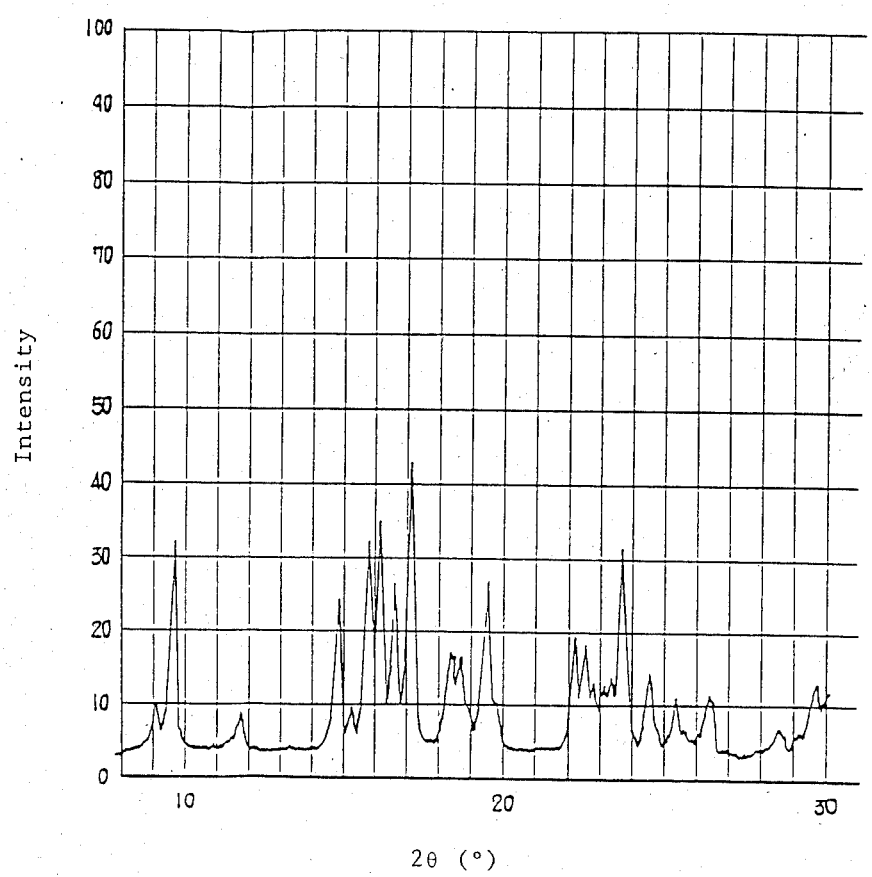
FIG. 3 shows an x-ray diffraction figure of crystalline maltopentaose.
Figure 4:
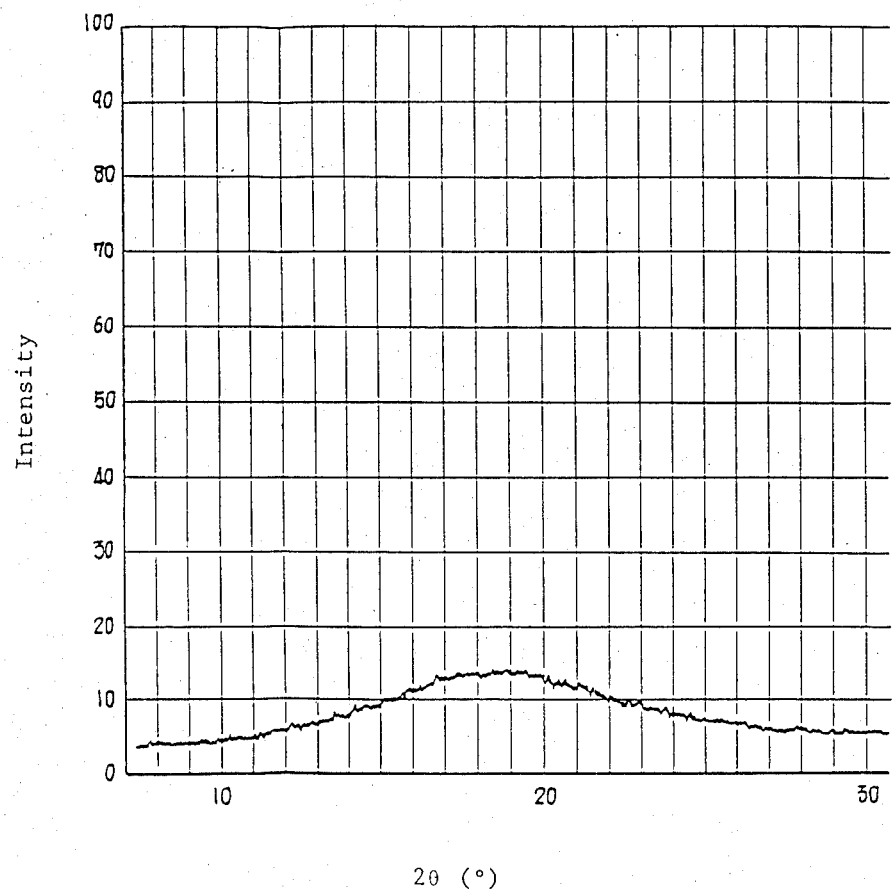
FIG. 4 shows an x-ray diffraction figure of amorphous pulverulent maltopentaose used as the control.

As shown in FIG. 3, upon x-ray diffraction analysis of the crystalline maltopentaose with CuKα ray, the x-ray diffraction figure had predominant diffraction angles (2θ) of 9.7°, 15.8°, 16.2°, 17.2°, and 23.7°.

In addition to the use as the seed, the crystalline maltopentaose can be favorably used as the substrate for serum amylase assay, as well as in foodstuffs, pharmaceuticals, cosmetics, chemicals, etc.

EXAMPLE 2

Pulverulent solid containing crystalline maltopentaose

The saccharide mixture solution with the maltopentaose purity of 40.3%, obtained in Experiment 1, was used as the feed solution. "Dowex 50WX4 ($Mg^{2+}$)", a strongly-acidic cation exchange resin in an alkaline-earth metal form, with a degree of cross-linking of 4%, manufactured by Dow Chemicals Co., Midland, MI, USA, was chosen, and packed in fresh stainless steel columns of the same sizes and material as used in Example 1 to give a total bed depth of 30 m. While keeping the inside column temperature at 75° C., the feed solution was admitted to the column in an amount of 6.6 v/v % to the bed volume, and then fractionated by passing 75° C. water at a space velocity of 0.13. Thereafter, the resultant fractions were successively recycled to the columns similarly as above, followed by recovery of fraction C with a maltopentaose purity of 89.4%. The fraction was purified similarly as in Example 1, and concentrated to obtain an about 97% solution (70° C.). The solution was then fed to a crystallizer, added with 2% crystalline maltopentaose seed, obtained by the method in Example 1, crystallized for a period of time under gentle stirring, placed in a tray, and solidified by four day-standing at about 20° C. The resultant solid was pulverized with a pulverizer equipped with cutters, and then dehydrated to obtain a pulverulent solid containing crystalline maltopentaose.

The resultant pulverulent product is substantially non-hygroscopic and in easily handleable form.

Upon x-ray diffraction analysis of the product with CuKα ray, the x-ray diffraction figure had predominant diffraction angles (2θ) of 9.7°, 15.8°, 16.2°, 17.2°, and 23.7° similarly as that of the crystalline maltopentaose at Example 1.

The product can be favorably used in foodstuffs, pharmaceuticals, cosmetics, and chemicals.

While we have shown and described certain present preferred embodiments of the invention it is to be distinctly understood that the invention is not limited thereto but may be otherwise variously embodied within the scope of the following claims.

We claim:

1. Crystalline maltopentaose, which exhibits predominant diffraction angle (2θ) of 9.7°, 15.8°, 16.2°, 17.2°, and 23.7° upon x-ray diffraction analysis with CuKα ray.

2. A process for producing crystalline maltopentaose, comprising:
    (a) providing a saccharide mixture solution containing maltopentaose, along with a saccharide with a glucose polymerization degree of 6 or higher (saccharide L) and a saccharide with a glucose polymerization degree of 4 or lower (saccharide S);
    (b) sequentially admitting predetermined volumes of the saccharide mixture solution and water to a column of a strongly-acidic cation exchange resin in salt form;
    (c) sequentially separating the effluents from the column into the following fractions in the specified order:
    first fraction rich in saccharide L,
    second fraction rich in saccharide L, but highly contaminated with maltopentaose,
    third fraction rich in maltopentaose,
    fourth fraction rich in maltopentaose, but highly contaminated with saccharide S, and
    fifth fraction rich in saccharide S;
    (d) recovering the third fraction rich in maltopentaose;
    (e) crystallizing the maltopentaose; and
    (f) recovering the resultant crystalline maltopentaose.

3. The process in accordance with claim 2 wherein said crystalline maltopentaose exhibits predominant diffraction angles (2θ) of 9.7°, 15.8°, 16.2°, 17.2°, and 23.7° upon x-ray diffraction analysis with CuKα ray.

4. The process in accordance with claim 2 wherein the degree of cross-linking of the said strongly-acidic cation exchange resin is 6% or lower.

5. The process in accordance with claim 2 which comprises:
    (a) providing a saccharide mixture solution containing maltopentaose, along with saccharide L and saccharide S;
    (b) sequentially admitting predetermined volumes of the saccharide mixture solution and water to a column of a strongly-acidic cation exchange resin in salt form;
    (c) sequentially separating the effluents from the column into the following fractions in the specified order;
    first fraction rich in saccharide L,
    second fraction rich in saccharide L, but highly contaminated with maltopentaose,
    third fraction rich in maltopentaose,
    fourth fraction rich in maltopentaose, but highly contaminated with saccharide S, and
    fifth fraction rich in saccharide S;
    (d) recovering the third fraction rich in maltopentaose;
    (e) sequentially admitting into the column;
    the second fraction obtained in step (c),
    a saccharide mixture solution containing maltopentaose, along with saccharide L and saccharide S;
    the fourth fraction obtained in step (c), and water; and
    (f) repeating steps (c), (d) and (e) in a cyclic manner,
    (g) crystallizing the maltopentaose; and
    (f) recovering the resultant crystalline maltopentaose.

6. The process in accordance with claim 2, wherein the strongly-acidic cation exchange resin is in an alkali- or an alkaline earth-metal form.

7. The process in accordance with claim 2, wherein said saccharide mixture solution has been obtained by:
    gelatinizing starch;
    subjecting the resultant starch solution to the action of α-amylase; and
    purifying the resultant hydrolysate containing maltopentaose.

* * * * *